(12) United States Patent
Humphreys, Jr. et al.

(10) Patent No.: US 6,176,847 B1
(45) Date of Patent: Jan. 23, 2001

(54) SURGICAL IRRIGATION SYSTEM INCORPORATING FLOW SENSOR DEVICE

(75) Inventors: James E. Humphreys, Jr., Genoa City; Austin Braganza, Milwaukee, both of WI (US)

(73) Assignee: Circon Corporation, Santa Barbara, CA (US)

(*) Notice: Under 35 U.S.C. 154(b), the term of this patent shall be extended for 0 days.

(21) Appl. No.: 09/312,254

(22) Filed: May 14, 1999

(51) Int. Cl.[7] .................................................. A61M 5/00
(52) U.S. Cl. .............................................. 604/246; 604/30
(58) Field of Search .................................. 604/22, 30, 31, 604/32, 33, 34, 35, 246, 247, 248, 249, 253–254, 255

(56) References Cited

U.S. PATENT DOCUMENTS

| | | | |
|---|---|---|---|
| 3,042,038 | * 7/1962 | Beacham | 604/254 |
| 3,101,710 | * 8/1963 | Koehn | 604/254 |
| 4,256,103 | * 3/1981 | Mylrea | 604/254 |
| 4,648,869 | * 3/1987 | Bobo, Jr. | 604/246 |
| 5,093,593 | 3/1992 | Philipp . | |
| 5,470,305 | 11/1995 | Arnett et al. . | |
| 5,484,402 | 1/1996 | Saravia et al. . | |
| 5,520,652 | * 5/1996 | Peterson | 604/35 |
| 5,810,765 | * 9/1998 | Oda | 604/31 |

OTHER PUBLICATIONS

Millman and Halkias, Integrated Electronics, Analog and Digital Circuits and Systems, Sect. 2–6, pp. 31–32, 1972.*

* cited by examiner

Primary Examiner—Wynn Wood Coggins
Assistant Examiner—Manuel Mendez
(74) Attorney, Agent, or Firm—Bradley M. Ganz (57) ABSTRACT

A surgical irrigation system utilizing a flow sensor device; upon sensing fluid flow, the flow sensor device activates a fluid acceleration or pumping mechanism to pump fluid to a surgical site; the flow sensor device is capable of being conveniently located between an elevated source of fluid and a surgical handpiece; since the flow sensor device activates the pumping mechanism, the surgical handpiece is liberated from use of an electrical-type switch to activate the pumping mechanism, and, instead, is provided with a valve for mechanically starting and stopping fluid flow.

21 Claims, 6 Drawing Sheets

Fig. 7

SURGICAL IRRIGATION SYSTEM INCORPORATING FLOW SENSOR DEVICE

FIELD OF THE INVENTION

This invention relates to a surgical irrigation system which utilizes a liquid flow sensor device to activate a pump or impeller to increase fluid flow from a fluid source through a handpiece to a surgical site. The invention also relates to a device which is capable of activating a pump or impeller when the device senses the start of fluid flow.

DESCRIPTION OF THE PRIOR ART

The use of surgical irrigation systems is known in the art. Such systems typically comprise an irrigation liquid source and a handpiece which has an inlet port connected to the irrigation liquid source, and an outlet port connected to, for example, a probe extending to an operative site within a mammalian body.

In the past it has been typical that such a handpiece is provided with a hand actuable electrical switch which is electrically connected to a remotely located motor for driving a pump to start and maintain irrigation liquid flow through the handpiece. Further, it is common for such a handpiece to additionally be connected to a vacuum source for applying suction to the operative site. Thus, when used by a surgeon, the surgeon can direct the probe of the handpiece to a surgical site and, by use of an electric switch on the handpiece, selectively choose to switch either irrigation liquid or vacuum to the surgical site.

One prior art surgical irrigation system is disclosed in U.S. Pat. No. 5,470,305, which issued to Arnett et al. on Nov. 28, 1995. That patent is directed to a surgical irrigation system, and particularly to an irrigation handpiece with a built in pulsing pump. The handpiece is supplied with irrigation liquid by connecting a port on the handpiece to a source of irrigation liquid, utilizing a flexible tube. The pulsing pump, which is located within the handpiece, is provided with power by connecting the handpiece to a remotely located power supply (i.e., a battery pack) by running insulated electrical conductors along the flexible tubing which is connected to the source of irrigation liquid. The pump is activated by a switch on the handpiece. But convenience and ease of manipulation are interfered with by the presence of the electrical conductors running along the tubing and the weight of the pulsing pump in the handpiece.

Another surgical irrigation system is disclosed in U.S. Pat. No. 5,484,402, which issued to Saravia et al. on Jan. 16, 1996. Saravia et al. disclose a surgical irrigation system which provides the surgeon with the ability to selectively choose to supply either irrigation liquid or suction to a surgical site. The system comprises a remotely located source of irrigation liquid and a remotely located suction source (i.e., vacuum). Furthermore, the system also comprises a suction/irrigation probe assembly consisting of a hand-held handpiece having a forward protruding hollow tip for supplying either the irrigation liquid or vacuum to the surgical site. The assembly also includes a self-contained pumping unit remotely located from the handpiece to pump irrigation liquid to the handpiece, into the protruding hollow tip, and to the surgical site. The remotely located pumping unit comprises a power supply (i.e., a battery pack), which is activated by an electrical switch in the handpiece. Therefore, the self-contained pumping unit must be connected to the switch in the handpiece by running cumbersome electrical cable along the flexible tubing that connects the pumping unit to the electrical switch on the handpiece.

Although the art is replete with various other efforts to provide new, improved surgical irrigation systems, the search continues. We have now, for the first time, provided a new and improved surgical irrigation system which has much better portability, significantly lighter weight, and radically improved ease of use in the operating room.

SUMMARY OF THE INVENTION

The present invention relates to a surgical irrigation system not requiring any cumbersome electrical connection between the handpiece and the pump. The system handpiece does not include any electrical switch for activating a motor to drive a pump to start and maintain irrigation liquid flow. Its handpiece instead utilizes only a valve for starting and stopping liquid flow in combination with a sensitive, remotely located flow sensor which, by sensing even a trickle or a minor fluid flow, hydraulically activates a remotely located pump to pump a full volumetric flow of fluid to the surgical site. The flow sensor device is remotely located, not on the manually manipulable surgical handpiece, which needs to be of light weight, highly portable and easily manipulated by the surgeon.

The flow sensor device can include a large number of alternative designs, any of which is capable of sensing fluid flow through, for example, a chamber, and once sensing fluid flow, hydraulically activating a pumping mechanism or impeller to create the requisite full volume fluid flow. Such embodiments will become apparent to those skilled in the art upon reading the following detailed description of the invention and by studying the accompanying drawings.

DESCRIPTION OF THE PREFERRED EMBODIMENTS

The present invention is useful in surgical irrigation systems and encompasses a large number of alternative designs, any of which is capable of starting and sensing even a small amount of gravity or other fluid flow, and once sensing such small amount, activating a fluid accelerator.

The latter may be a pump or pumping mechanism or impeller of any type, to provide substantially immediately the full fluid flow of which the accelerator pump is capable. The invention also provides surgical irrigation systems which utilize a novel lightweight handpiece working with one or more novel flow sensor devices without using cumbersome wiring and without interfering with easy and quick handpiece manipulation by the surgeon.

The invention provides a simple, easily maneuverable handpiece which does not contain any electrical switch connected by wires to a pump or pump motor. Rather, the handpiece is provided with a means capable of mechanically starting and stopping fluid flow by instituting a small flow of an initially valve-actuated fluid through the handpiece.

A non-limiting example is a hand controllable valve conveniently located at the handpiece. The valve can be of very simple design and only needs to provide the surgeon with the ability to open or close the valve and thus, start or stop fluid flow hydraulically through the handpiece. The valve on the handpiece need only be capable of starting a minor amount of fluid flow (i.e., a trickle) when the valve is opened. Once having detected even a minor fluid flow, it immediately activates the flow accelerator to provide full fluid flow quickly to the surgical site.

To fully understand the breadth of the present invention, reference is made to non-limiting examples of particularly preferred embodiments of the present invention. They are described below with reference to the figures.

Figure 1:
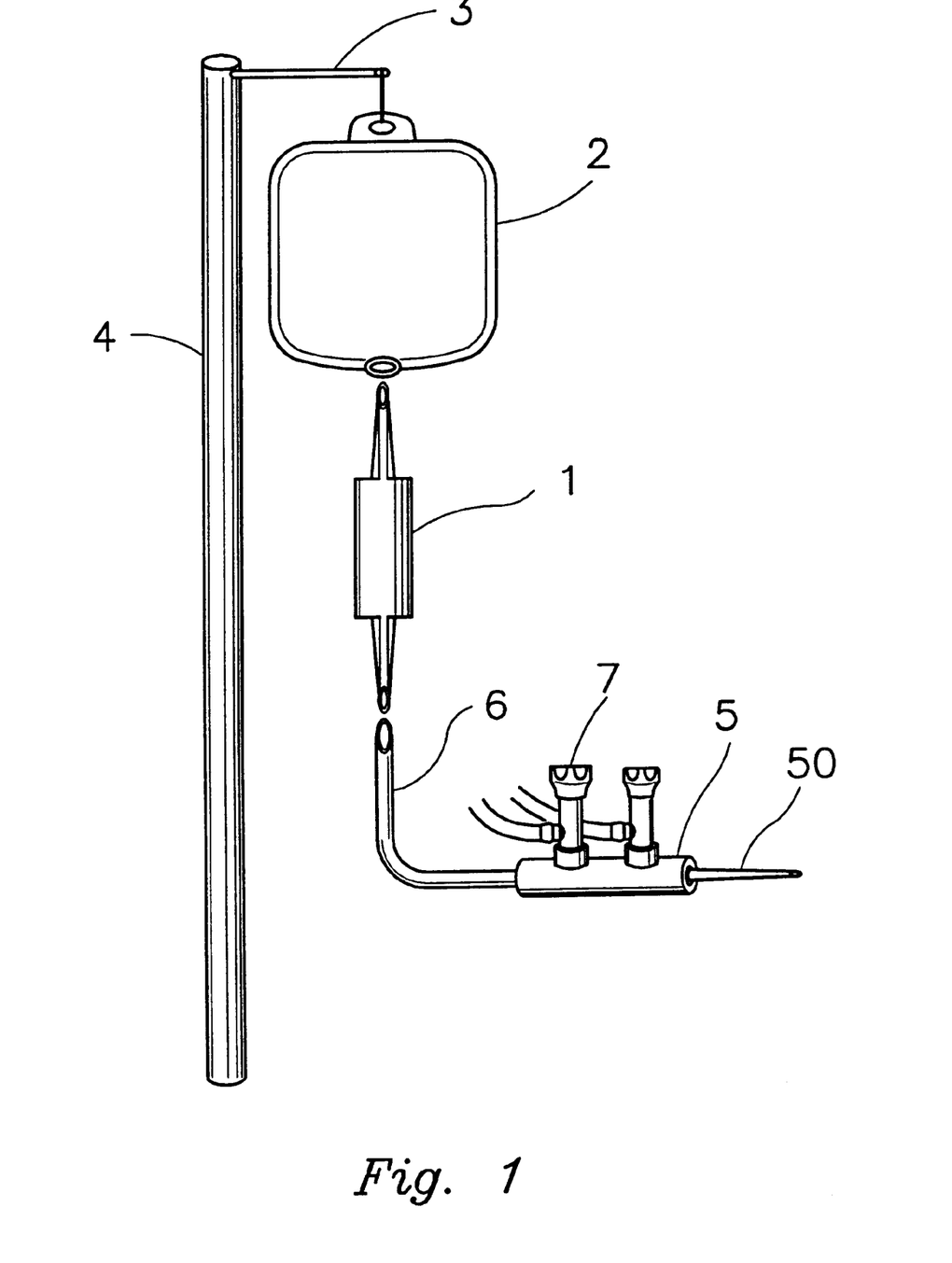
FIG. 1 is a schematic drawing of a representative surgical irrigation system of the present invention.

A representative surgical irrigation system of the present invention is illustrated in FIG. 1 which shows a fluid source that may be located in a conventional manner, e.g., by utilizing a bag 2 containing fluid supported by a horizontal arm 3 adjustably fixed on a vertically standing pole 4 in a manner such that the bag 2 is spaced apart from and at a level above the handpiece 5. The fluid is supplied to the handpiece 5 by providing a flexible conduit such as elongate flexible tubing 6 running from the outlet of the fluid source to the handpiece. The flow sensor device 1, as shown, is directly connected to and supported at the fluid source, and is not located on the handpiece 5. Flow sensor device 1 may alternatively be adjustably fixed and supported on vertically standing pole 4. The outlet from the flow sensor device 1 is then connected to an inlet of an easily portable handpiece 5 by utilizing, for example, a flexible conduit such as elongate flexible tubing 6.

Handpiece 5 is supplied with probe 50, capable of entering into the operative site, allowing the surgeon to deliver fluid to the surgical site. Handpiece 5 is also supplied with a hand controllable valve 7, here shown as a trumpet valve, capable of starting and stopping gravity flow of fluid from the elevated bag 2, through the flow sensor 1. Once the surgeon opens the valve 7 to start gravity flow of fluid, the flow sensor device 1, sensing flow of the fluid, activates the impeller or fluid accelerator, which in one embodiment is conveniently located within the flow sensor device 1, to increase fluid flow. The pump or impeller may be located remote from said flow sensor device as well, but they are both conveniently carried by the pole 4.

The surgeon may stop fluid flow by simply closing valve 7 on handpiece 5. The remotely located flow sensing device 1, now sensing the stoppage of fluid flow, acts to turn off the pump or impeller as will be described in further detail.

Handpiece 5 may also be connected to a suction source, and handpiece 5 can be designed to allow the surgeon to easily select between supplying fluid, such as irrigation liquid, or vacuum to a surgical site, using connecting tubing shown leading into the two trumpet valves shown in FIG. 1. Such trumpet valves are fully shown and described in the co-pending U.S. application Ser. No. 08/889,645 filed Jul. 8, 1997, assigned to the assignee hereof, the disclosure of which is hereby incorporated by reference.

The flow sensor device 1 of the present invention can be generally characterized as having a fluid flow chamber which has an inlet port connected to a source of fluid and an outlet port which may be connected to an inlet portion of a suitable surgical handpiece. Within the fluid flow chamber is located a suitable flow detector which is sensitive to fluid flow. The flow sensor additionally comprises a conventional or proprietary trumpet valve for opening or closing gravity flow. The motor is provided with an activator to be described in detail, to activate a motor which in turn drives a pump or impeller to increase fluid flow.

Figure 2:
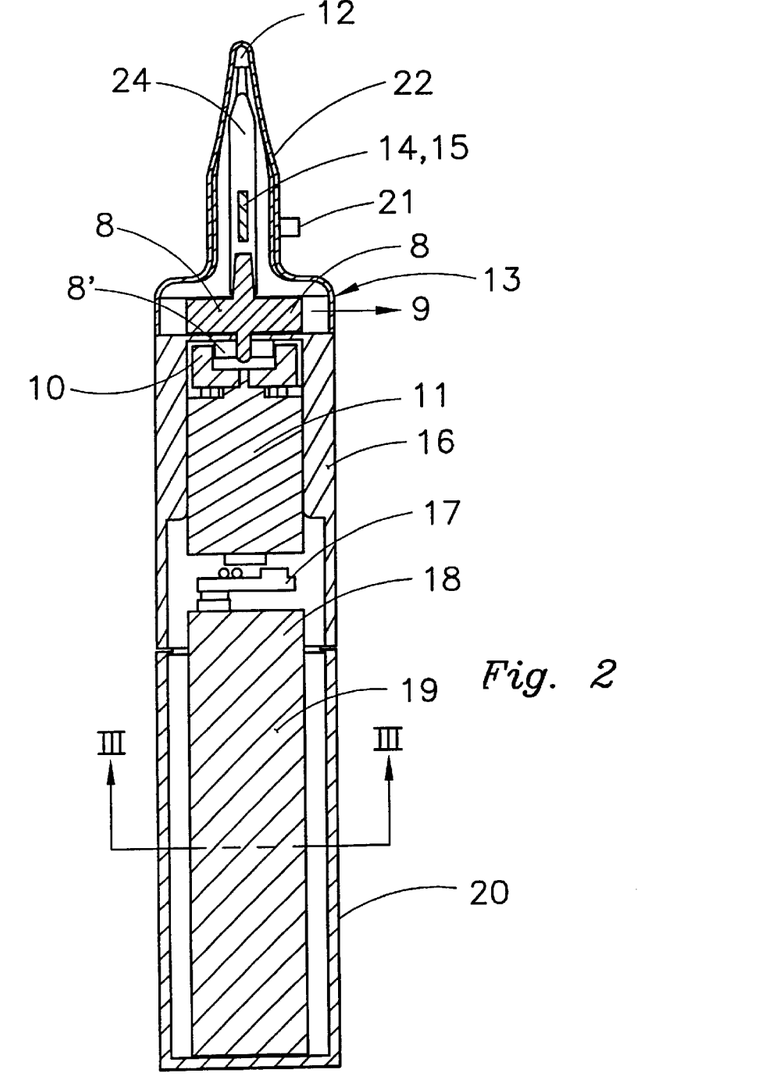
FIG. 2 is a schematic cross section of a preferred flow sensor device.
Figure 3:
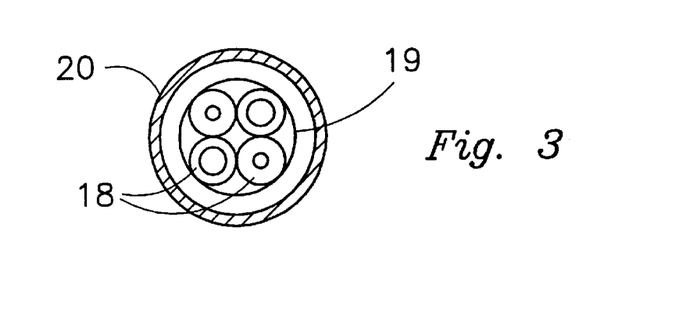
FIG. 3 is a cross section of FIG. 2 taken at line III—III of FIG. 2.

FIG. 2 is a schematic cross section of one specific preferred flow sensor device 1 of the present invention which is provided with a sensor housing that has an inlet passage 12 containing a buoyant capsule 14 which additionally carries a magnet 15. The magnet 15 is shown located within the capsule 14 but may be located on an outer surface thereof, or elsewhere. The buoyant capsule 14 is located within fluid flow chamber 24. A Hall-Effect switching circuit board and Hall-Effect sensor 21 are attached to flow sensor device 1 but outside of fluid flow chamber 24 and at a selected distance below inlet passage 12. Hall-Effect switching circuit is connected to motor 11 by conventional electric wires (not shown). The motor 11 is powered by any conventional means, for example, by batteries 18 operating through circuit board 17. Outlet port 9 is connected by fluid flow tubing to the surgical handpiece 5 (FIG. 1), which carries the valve 7 for starting and stopping fluid flow. Since the flow sensor device 1 of FIG. 2 utilizes a buoyant capsule 14 as a means that swings up and down in response to fluid flow, it is preferable that during operation, the device be arranged in an at least partial vertical position.

As one skilled in the art will now understand, as a trickle of fluid enters inlet passage 12, buoyant capsule 14 is displaced downward toward the bottom of fluid flow chamber 24. As buoyant capsule 14 reaches a position in the fluid flow chamber 24 substantially even with the location of Hall-Effect sensor 21, magnet 15 located on or within buoyant capsule 14 activates the Hall-Effect sensor 21 which in turn activates the Hall-Effect circuit, which in turn activates motor 11. Motor 11 then drives impeller 8. As impeller 8 turns the flow within fluid flow chamber 24 is accelerated to the desired flow rate. When the surgeon wishes to stop the flow of fluid, the surgeon needs no electric switch but merely has to close the valve 7 on the handpiece 5. Flow within the fluid flow chamber 24 is then stopped and buoyant capsule 14 rises again to the upper portion of the fluid flow chamber 24, thus deactivating the Hall-Effect switching circuit and motor 11.

Figure 7:
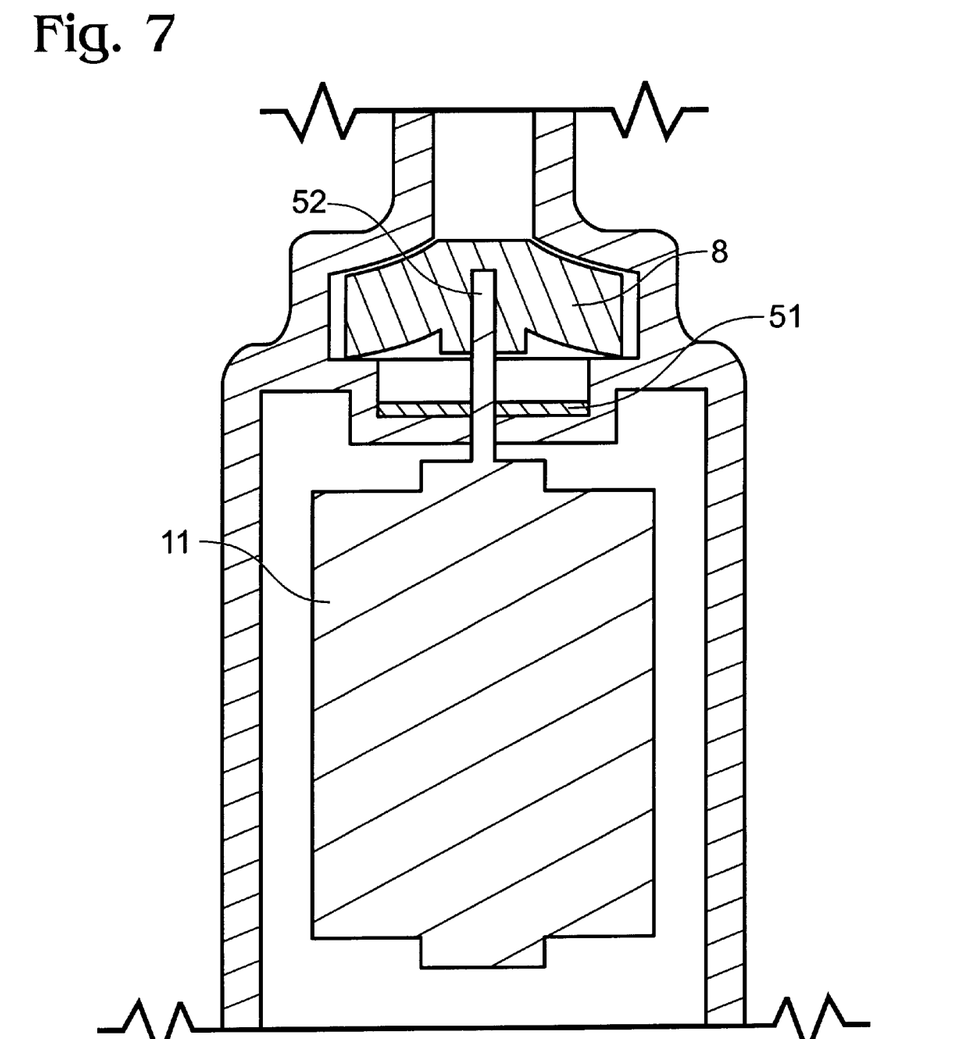
FIG. 7 is a schematic cross section of an alternate embodiment of the flow sensor device in accordance with this invention.

Motor 11 may be coupled to impeller 8 using a magnetic coupling configuration as shown in FIG. 2. Motor 11 may also be coupled to impeller 8, as shown in FIG. 7, using a shaft 52 and motor configuration employing a seal 51 between the motor 11 and impeller 8.

Preferably, buoyant capsule 14 is large enough in diameter so that when fluid flow is stopped, and buoyant capsule 14 rises to the top of fluid flow chamber 24, the buoyant capsule 14 is capable of providing a seal around inlet port 12 to prevent backflow of fluid out of fluid flow chamber 24. Additionally, it is sometimes desirable to include ribs, protuberances or the like spaced about the inner surface of fluid flow chamber 24 at the lower end thereof to prevent buoyant capsule 24 from sealing off fluid flow through the bottom portion of fluid flow chamber 24.

Figure 4A:
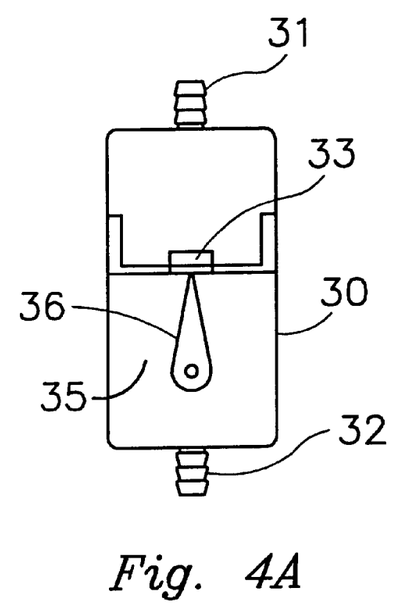
FIG. 4A is a schematic cross section showing one form of a flow sensor device in accordance with this invention, shown in a position detecting no fluid flow.
Figure 4B:
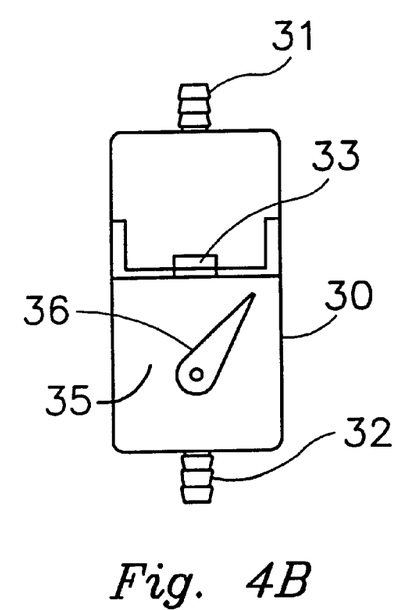
FIG. 4B is a schematic cross section of the device shown in FIG. 4A wherein the device is shown in a position detecting fluid flow.

FIG. 4A and FIG. 4B are schematic cross sections of another preferred embodiment of the present invention. For simplicity and brevity, these figures do not show the usual batteries, motor, and impeller, which are depicted in FIG. 2. FIG. 4A shows a flow sensor device 30 which utilizes a buoyant, vertical paddle 36 as a means sensitive to fluid flow. When the fluid within fluid flow chamber 35 is static the buoyant vertical paddle 36 is oriented in the vertical position as shown. Inlet port 31 is located at one end of flow sensor device 30 and outlet port 32 is located at the opposite end of flow sensor device 30. Switch 33 is connected to a motor which drives an impeller or pump to accelerate fluid flow. FIG. 4B shows flow sensor device 30 when fluid is flowing through fluid flow chamber 35. As can be seen, buoyant vertical paddle 36 is forced to one side as fluid flows through fluid flow chamber 35. As buoyant vertical paddle 36 moves to one side, disconnecting from switch 33, switch 33 activates the motor which in turn drives the impeller or pump to increase fluid flow. When fluid flow is stopped, buoyant vertical paddle 36 returns to the vertical orientation and reconnects with switch 33, which in turn deactivates the motor.

Figure 5A:
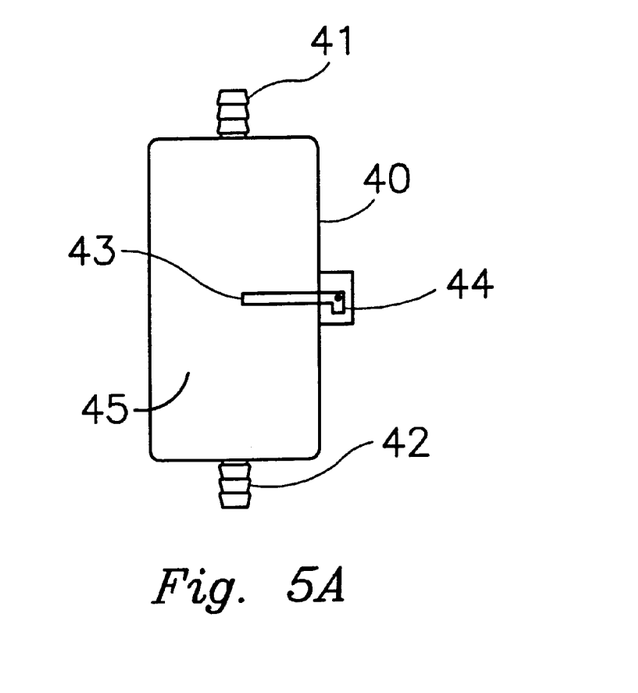
FIG. 5A is a schematic cross section of another form of a flow sensor device, which is shown in a position detecting no fluid flow.
Figure 5B:
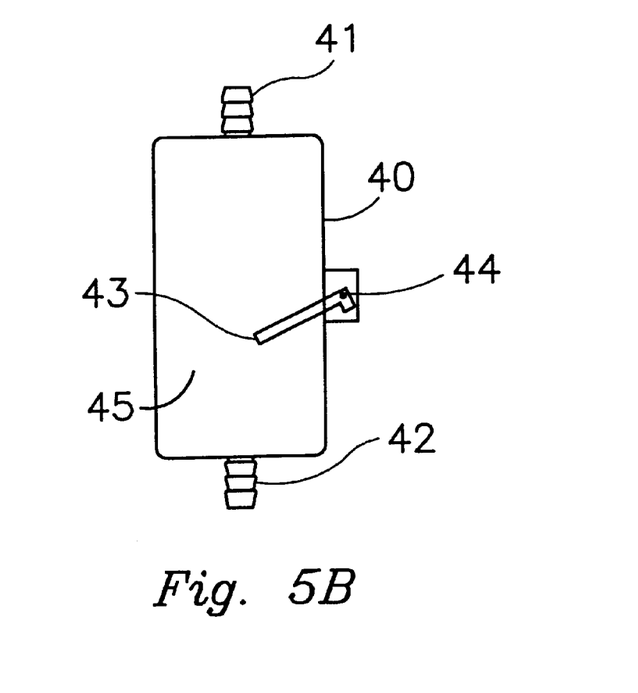
FIG. 5B is a schematic cross section of the device of FIG. 5A, wherein the device is shown in a position detecting fluid flow.

FIG. 5A and FIG. 5B show still another preferred embodiment of the flow sensor device of the present invention. As depicted in FIGS. 5A and 5B, the flow sensor device 40 has at one end thereof an inlet port 41 and at the other end thereof, an outlet port 42. Located within fluid flow chamber 45 is a horizontal paddle 43 which serves as the means sensitive to fluid flow. Horizontal paddle 43 is contacted with switch 44. As fluid trickles through fluid flow chamber 45, horizontal paddle 43 is swung down and toward outlet port 42, and switch 44 activates the motor which in turn drives the impeller or pump. When fluid flow is interrupted, horizontal paddle 43 returns to the horizontal position and switch 44 deactivates the motor.

Figure 6:
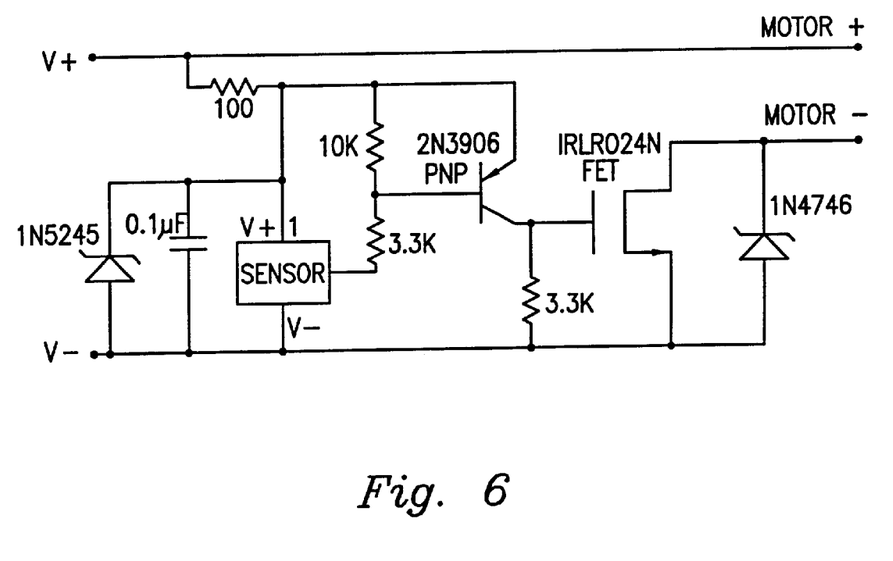
FIG. 6 is a schematic diagram of a "Hall-Effect" switching circuit which is an embodiment of this invention and can be utilized in the flow sensor device of FIG. 1 and FIG. 2.

FIG. 6 is a circuit diagram showing one of many appropriate components and one preferred way they may be connected to a motor for battery operation between voltages $V_+$ and $V_-$. The word "sensor" in the diagram may preferably be a "Hall Effect" sensor as previously described.

The flow sensor device of the present invention provides for a large number of advantageous design opportunities for surgical irrigation systems. For example, it is possible to locate the flow sensor device outside of a surgical handpiece, yet allow for the use of a pump or the equivalent to increase fluid flow, all without requiring an electrical connection between the handpiece and flow sensor device. The handpiece only need be provided with a means for mechanically starting and stopping flow of fluid, such as a valve or the like. This, of course, offers design flexibility when designing the handpiece, which can be designed without regard to burdening the handpiece, and without locating a pump within the handpiece, and also without regard to providing any electrical connections from the handpiece to a pump. Thus, the surgical irrigation systems of the present invention allow for lightweight, attractively designed handpieces which are easily maneuverable due to, among other things, their light weight and lack of electrical connections between the handpiece and the remotely located pump.

It will be appreciated that considerable choice is available for the specific flow sensor. It may be, as previously discussed, the preferred Hall Effect sensor or, for example, a vertical paddle or a horizontal paddle, or a magnetic sensor. The magnetic sensor could comprise a magneto resistive sensor which is sensitive to a magnet. Further examples include a disposable irrigation pump having a floatable capsule to detect the flow, a pair of spaced-apart conductive plates capable of electrically sensing the movement of the fluid, a submerged paddle wheel connected to operate in conjunction with an LED/detector assembly which detects the rotation of the paddle wheel in response to fluid flow, a thermal dispersion flow switch having heated sensor and a spaced-apart non-heated sensor and capable of sensing fluid flow from one sensor to the other, and a pressure switch/force switch having a curved surface responsive to the fluid flow. Various other floatable detectors may be used, including a rotaball switch traveling up and down between spaced apart stops in order to actuate an LED receiver. The flow sensor may also comprise a photo optical sensor device having a light emitting diode, a photocell, and a reflecting mirror having a gray scale. The reflecting mirror of the photo optical sensor device may be mounted on a floatable capsule. Many other flow detecting devices can be adapted.

The above-described preferred embodiments should not be viewed as limiting the present invention and should only be viewed as illustrative of the many different embodiments which are encompassed by the present invention. After studying the above disclosure, one skilled in the art will now recognize the numerous different embodiments which are encompassed by the present invention.

What is claimed is:

1. A surgical irrigation system comprising:

a manually moveable handpiece having an inlet and an outlet for fluid, said handpiece being adapted for use by a surgeon adjacent a fluid source located at a position spaced apart from and at a level that is higher than said handpiece;

a flexible conduit extending from said fluid source to said handpiece to allow for feed of fluid to said handpiece;

a flow sensor device supported adjacent said fluid source, said flow sensor device having an inlet port, an outlet port, fluid flow chamber, switch means sensitive to fluid flow capable of activating and deactivating a fluid accelerator in communication with the fluid source which causes increased fluid flow through said handpiece and to said surgical site; and handpiece control means carried by said handpiece to open and close flow of said fluid from said handpiece, whereby initiation of gravity flow by said handpiece hydraulically activates said switch means associated with the fluid chamber causing said switch means to activate said accelerator to increase the fluid flow rate through said handpiece.

2. The surgical irrigation system of claim 1, wherein said handpiece is connected to a suction source.

3. The surgical irrigation system of claim 1, wherein said switch means sensitive to fluid flow comprises a buoyant capsule.

4. The surgical irrigation system of claim 3, wherein said switch means further comprises a Hall-Effect switching circuit.

5. The surgical irrigation system of claim 1, wherein said switch means sensitive to fluid flow comprises a buoyant paddle.

6. The surgical irrigation system of claim 1, wherein said switch means sensitive to fluid flow comprises a paddle arranged horizontally relative to said inlet port and said outlet port.

7. The surgical irrigation system of claim 1, wherein said handpiece control means comprises a valve.

8. The surgical irrigation system of claim 1, wherein said switch means sensitive to fluid flow is a floatable capsule to detect the flow.

9. The surgical irrigation system of claim 1, wherein said switch means sensitive to fluid flow is a spaced apart conductive plate.

10. The surgical irrigation system of claim 1, wherein said switch means sensitive to fluid flow is a submerged paddle wheel.

11. The surgical irrigation system of claim 1, wherein said switch means sensitive to fluid flow is a heated sensor and spaced-apart non-heated sensor.

12. The surgical irrigation system of claim 1, wherein said switch means sensitive to fluid flow is a pressure switch having a movable surface.

13. The surgical irrigation system of claim 1, wherein said switch means sensitive to fluid flow comprises a magnetic sensor.

14. The surgical irrigation system of claim 13, wherein said magnetic sensor comprises a magneto resistive sensor sensitive to a magnet.

15. A flow sensor device connected to a surgical suction or irrigation system for performing suction or irrigation at an operative site in a surgical patient, comprising:

a fluid flow chamber having an inlet port connected to a fluid source and an outlet port connected to provide fluid to said operative site;

detection means in said flow chamber, said detection means being sensitive to fluid flow through said chamber; and switch means operative in response to said detection means for activating and deactivating an accelerator to increase the flow of said fluid through said fluid flow chamber and to said surgical system.

16. The flow sensor device of claim 15, wherein said detection means comprises a buoyant capsule.

17. The flow sensor device of claim 16, wherein said detection means further comprises a Hall-Effect switching circuit.

18. The flow sensor device of claim 15, wherein said detection means comprises a buoyant paddle.

19. The flow sensor device of claim 15, wherein said detection means comprises a paddle arranged horizontally relative to said inlet port and said outlet port.

20. The flow sensor device of claim 14, wherein said detection means comprises a magnetic sensor.

21. The flow sensor device of claim 20, wherein said magnetic sensor comprises a magneto resistive sensor sensitive to a magnet.

\* \* \* \* \*